(12) United States Patent
Jin et al.

(10) Patent No.: US 9,725,390 B2
(45) Date of Patent: Aug. 8, 2017

(54) INTEGRATED PROCESS FOR CONVERTING METHANE TO AROMATICS AND OTHER CHEMICALS

(71) Applicant: SAUDI BASIC INDUSTRIES CORPORATION, Riyadh (SA)

(72) Inventors: Yaming Jin, Owasso, OK (US); Majed M. Mussa, Riyadh (SA); Syed A. Hashmi, Riyadh (SA); Flaiyh F. Al-Anazi, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/027,567

(22) PCT Filed: Oct. 7, 2014

(86) PCT No.: PCT/US2014/059442
§ 371 (c)(1),
(2) Date: Apr. 6, 2016

(87) PCT Pub. No.: WO2015/054212
PCT Pub. Date: Apr. 16, 2015

(65) Prior Publication Data
US 2016/0251293 A1   Sep. 1, 2016

Related U.S. Application Data

(60) Provisional application No. 61/888,305, filed on Oct. 8, 2013.

(51) Int. Cl.
*C07C 45/50* (2006.01)
*C01B 3/38* (2006.01)
(Continued)

(52) U.S. Cl.
CPC ............. *C07C 45/50* (2013.01); *C01B 3/34* (2013.01); *C01B 3/38* (2013.01); *C01B 3/384* (2013.01);
(Continued)

(58) Field of Classification Search
CPC .... C01B 2203/0233; C01B 2203/0238; C01B 2203/06; C01B 2203/061; C01B 3/38;
(Continued)

(56) References Cited

U.S. PATENT DOCUMENTS 7,795,490 B2   9/2010   Iaccino et al.
8,378,162 B2   2/2013   Iaccino et al.
(Continued)

FOREIGN PATENT DOCUMENTS

WO   2006068814 A2   6/2006
WO   2010104762 A1   9/2010
WO   2013144735 A1   10/2013

OTHER PUBLICATIONS

Cui et al., "The effect of zeolite particle size on the activity of Mo/HZSM-5 in non-oxidative methane dehydroaromatization", Applied Catalysis A: General, 2011, vol. 393, pp. 348-358.
(Continued)

*Primary Examiner* — Jafar Parsa
(74) *Attorney, Agent, or Firm* — Cantor Colburn LLP

(57) ABSTRACT

Systems and methods for integrated production of aromatics and other chemicals are described. Systems and methods may include a process for producing benzene, methanol, butanals, dimethyl ethers, olefins and other chemicals that includes providing methane to a first reactor to produce a first product stream comprising benzene and hydrogen; recovering benzene and mixing the first product stream with a carbon dioxide and/or steam feed stream; providing the combined benzene depleted first product stream and carbon
(Continued)

dioxide and/or steam feed stream to a second reactor to produce a second product stream comprising synthesis gas, water and unconverted methane and carbon dioxide; and providing the synthesis gas to a third reactor to produce a third product stream comprising methanol, butanals, and other chemicals.

10 Claims, 1 Drawing Sheet

(51) Int. Cl.
| | |
|---|---|
| *C07C 2/76* | (2006.01) |
| *C07C 29/151* | (2006.01) |
| *C07C 41/01* | (2006.01) |
| *C10G 2/00* | (2006.01) |
| *C01B 3/34* | (2006.01) |

(52) U.S. Cl.
CPC ............ *C07C 2/76* (2013.01); *C07C 29/1518* (2013.01); *C07C 41/01* (2013.01); *C10G 2/32* (2013.01); *C10G 2/50* (2013.01); *C01B 2203/0233* (2013.01); *C01B 2203/0238* (2013.01); *C01B 2203/06* (2013.01); *C01B 2203/061* (2013.01); *C01B 2203/062* (2013.01); *C01B 2203/1241* (2013.01); *C10G 2300/1081* (2013.01); *C10G 2300/1096* (2013.01); *C10G 2400/30* (2013.01); *Y02P 20/125* (2015.11)

(58) Field of Classification Search
CPC C07C 41/01; C07C 45/50; C07C 2/76; C07C 15/04; C07C 29/1518; C07C 31/04; C07C 47/02; C07C 43/043; C10G 2/32; C10G 2/50; C10G 2400/30; C10G 2300/1081
See application file for complete search history.

(56) References Cited

U.S. PATENT DOCUMENTS

| | | |
|---|---|---|
| 2008/0021251 A1 | 1/2008 | Iaccino et al. |
| 2010/0016647 A1 | 1/2010 | Yamada et al. |
| 2011/0172089 A1 | 7/2011 | Ogawa |
| 2013/0030063 A1 | 1/2013 | Randhava et al. |

OTHER PUBLICATIONS

Xu et al.,"Comparison of the activities of binder-added and binder-free Mo/HZSM-5 catalysts in methane dehydroaromatization at 1073 K in periodic CH4-H2 switch operation mode", Journal of Natural Gas Chemistry, 2012, vol. 21, pp. 729-744.
International Search Report for International Application No. PCT/US2014/059442; Date of Mailing: Jan. 14, 2015; 5 pages.
Written Opinion of the International Searching Authority for International Application No. PCT/US2014/059442; Date of Mailing: Jan. 14, 2015; 7 pages.

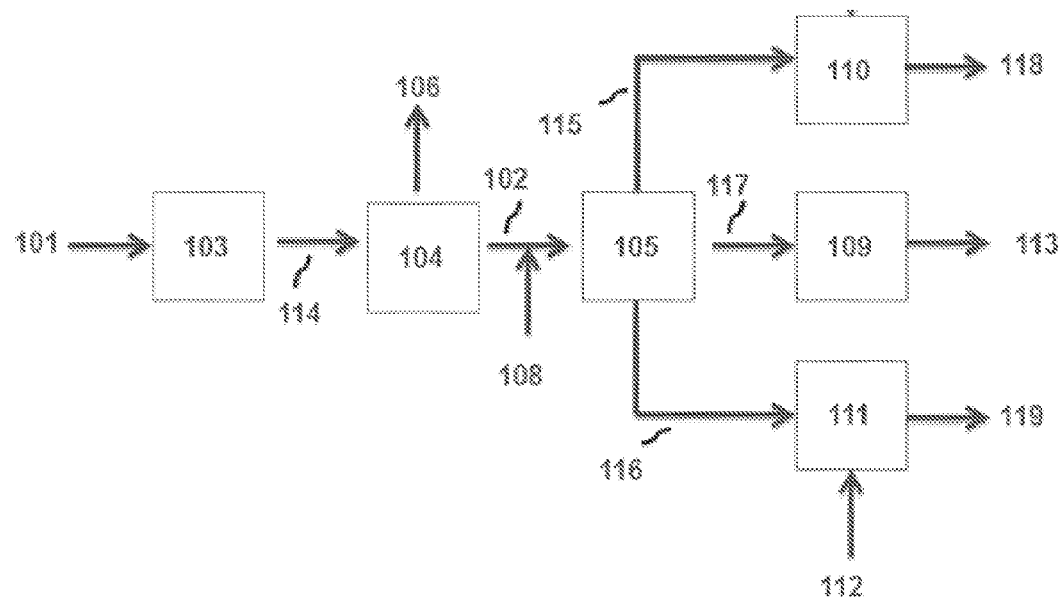

INTEGRATED PROCESS FOR CONVERTING METHANE TO AROMATICS AND OTHER CHEMICALS

CROSS REFERENCE TO RELATED APPLICATIONS

This application is a 371 of International Application No. PCT/US2014/059442, filed Oct. 7, 2014, which claims priority to U.S. Provisional Application No. 61/888,305 filed Oct. 8, 2013, both which are incorporated herein by reference in their entirety.

TECHNICAL FIELD

The present invention relates to systems and methods for producing aromatics, methanol, and other chemicals, and more specifically, to integrated systems and methods for producing benzene, methanol, oxoproducts, and other value added chemicals in an integrated process.

BACKGROUND

Benzene and methanol are two essential commodity chemicals for chemical industries. Butanals (butyraldehydes), butanols, dimethyl ether (DME), as well as other chemicals, are value added performance chemicals.

Benzene ($C_6H_6$) has traditionally been obtained from petroleum feed sources. Industrial benzene production generally uses one of the following chemical processes: catalytic reforming, toluene hydrodealkylation, toluene disproportionation, and naphtha steam cracking. Traditional processes are becoming less economically viable as petroleum feed sources become more expensive. Natural gas is poised to replace petroleum feed sources as the primary source material used by the petrochemical industry. Direct conversion of methane ($CH_4$) to aromatics produces benzene at very high selectivity, with hydrogen as the main by-product. The separation of hydrogen from the benzene product, however, requires an expensive separation process, typically cryogenic separation, pressure swing adsorption (PSA), or both.

Methanol ($CH_3OH$) is the simplest alcohol. The most significant use of methanol is in the production of other chemicals. In many instances, methanol is produced from synthesis gas (syngas). Synthesis gas is a fuel/gas mixture composed mainly of hydrogen, carbon monoxide, and usually small quantities of carbon dioxide. Methanol may be produced from synthesis gas in a catalytic industrial process directly from carbon monoxide, carbon dioxide, and hydrogen. To produce methanol, carbon monoxide and hydrogen react over a catalyst. The most commonly used catalyst is a mixture of copper, zinc oxide, and alumina, and produces methanol with a high selectivity as per the following formulas:

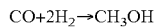

$$CO + 2H_2 \rightarrow CH_3OH$$

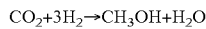

$$CO_2 + 3H_2 \rightarrow CH_3OH + H_2O$$

Hydroformylation of a syngas stream with a propylene stream may provide an oxo-aldehydes (butanals) stream that can be used for production of oxo-alcohols (butanols). Hydroformylating the propylene stream and the syngas stream may provide an aldehyde stream including n-butanal (NBAL) and isobutanal (IBAL). Hydrogenating the aldehyde stream may produce corresponding alcohol streams.

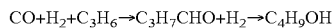

$$CO + H_2 + C_3H_6 \rightarrow C_3H_7CHO + H_2 \rightarrow C_4H_9OH$$

Processes for the production of methanol and butyraldehydes, however, are not typically integrated with other systems and may not utilize alternative feed stocks.

Needs exist for improved systems and methods for increasing efficiency of feed stock conversion to benzene, methanol, butyraldehydes and other value added chemicals.

SUMMARY

A process for producing aromatics and other chemicals, comprises: providing methane to a first reactor to produce a first product stream comprising benzene and hydrogen; recovering benzene from the first product stream and mixing the remaining first product stream with a carbon dioxide or steam feed stream to create a combined product stream; providing the combined product stream comprising methane, C2's, C3's, and carbon dioxide or steam to a second reactor to produce a second product stream comprising synthesis gas, water, unconverted methane and carbon dioxide; and providing the synthesis gas to a third reactor to produce a third product stream comprising methanol, butanal, olefins, or dimethyl ether Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 1 shows an exemplary system for integrated conversion of feed stock to benzene, methanol, olefins, oxo products, Fischer-Tropsch (FT) products and other aromatics.

DETAILED DESCRIPTION

Systems and methods are described for integrated processes for the conversion of feed stocks, such as methane and carbon dioxide, to benzene, methanol, olefins, oxo products, Fischer-Tropsch (FT) products, and other aromatics. The processes described herein are exemplary processes only and used for illustrative purposes. Other variations and combinations of steps and components may be used as necessary.

Embodiments of the present invention solve many of the problems and/or overcome many of the drawbacks and disadvantages of the prior art by providing systems and methods for producing benzene, methanol, butanals and other chemicals in an integrated process. Embodiments of the present invention may include systems and methods for producing benzene, methanol and other chemicals in an integrated process. The systems and methods may include a process for producing benzene, methanol, olefins, oxo products, Fischer-Tropsch (FT) products and other aromatics.

The method may include providing methane to a first dehydroaromatization reactor to produce a first product stream comprising benzene, hydrogen, C2's, C3's and methane; recovering benzene from the product stream; mixing the remaining first product stream with a carbon dioxide feed stream; providing the combined first product stream coming from separator or extractor and carbon dioxide feed stream to a reforming reactor to produce a second product stream comprising synthesis gas; providing the synthesis gas to a synthesis reactor or oxo reactor to produce a product stream comprising methanol, dimethyl ether and/or butanals.

In certain embodiments, the synthesis gas coming from the reforming reactor may be used to produce different products such as olefins, dimethyl ether (DME), oxo products, FT products and aromatics.

In certain embodiments of the present invention, an integrated process may be divided into different components. FIG. 1 is a flow diagram illustrating an exemplary integrated process of the current invention.

In a first component of an exemplary integrated process, methane coming from feed line 101 may be converted to benzene and hydrogen via a dehydroaromatization reaction in reactor 103. The product stream coming from reactor 103 via line 114 goes to a separator 104. The benzene product is recovered from the separator 104 via line 106. In a subsequent component of an exemplary integrated process, the reaction product of the dehydroaromatization reaction, except the recovered benzene, then is sent via transfer line 102. A feed containing carbon dioxide and steam (water) is added via line 108 and mixed with the reaction product of the dehydroaromatization reaction, except the recovered benzene, to the transfer line 102. The combined stream may then be fed to a reforming reactor 105 to produce a product stream of synthetic gas.

In another component of an exemplary integrated process, the synthetic gas coming from reactor 105 may be routed to a methanol synthesis reactor 109 via transfer line 117 for conversion to methanol, which is sent out via methanol product line 113.

In another component of an exemplary process, the synthetic gas coming from reactor 105 may be routed to a dimethyl ether (DME) synthesis reactor 110 via transfer line 115 for conversion to DME, which is sent out via DME product line 118, and/or the synthetic gas coming from reactor 105 may be routed to a butanol synthesis reactor for conversion to butanol by hydroformylation with propylene.

In another component of an exemplary process the synthetic gas coming from reactor (105) may be routed to a hydroformylation reactor 111 via transfer line 116 for conversion to oxoaldehydes (butyraldehydes), which may be sent out via product line 119. Propylene may be added to the reactor 111 via line 112.

Elimination of the need to separate the hydrogen from the output stream of the dehydroaromatization reaction adds significant value to the exemplary integrated process by reducing time, cost and energy requirements. The hydrogen and other byproducts of the dehydroaromatization reaction can be reacted with added carbon dioxide and/or steam in a reforming reactor to produce synthesis gas in quantitative yields, which can then be used as a feed stock for creation of methanol and other chemicals. The integrated process brings considerable savings by avoiding costly hydrogen separation steps and improving energy/site efficiency by producing other valuable downstream products, such as methanol, DME and other aromatics.

As noted above, FIG. 1 is a flow diagram illustrating an exemplary integrated process of the current invention.

A feed stock of methane may be introduced into a first reactor 103. Any methane-containing feedstock can be used in the present process but, in general, the present process may be used with a natural gas feedstock. Other suitable methane-containing feedstocks may include those obtained from sources such as coal beds, landfills, agricultural or municipal waste fermentation, or refinery gas streams. Methane-containing feedstocks, such as natural gas, typically contain carbon dioxide and ethane in addition to methane. Ethane and other aliphatic hydrocarbons that may be present in the feedstock can, of course, be converted to desired aromatic products in a dehydroaromatization step. In addition, as will be discussed below, carbon dioxide can also be converted to useful syngas. Nitrogen and sulfur impurities are also typically present in methane-containing streams and may be removed or reduced to acceptable levels prior to use of the streams as disclosed herein. In certain embodiments, the feed to the dehydroaromatization step may contain less than approximately 100 parts per million (ppm), less than approximately 10 ppm, or less than approximately 1 ppm each of nitrogen and sulfur compounds.

Generally, the feedstock lower molecular weight hydrocarbon of the present invention may include methane or natural gas containing $C_1$ to $C_4$ hydrocarbons. In certain embodiments, the feed to the dehydroaromatization step may include approximately 95 to approximately 99.9 mole percent (mol %), more preferably 97 to approximately 99 mol % methane.

The first reactor may convert the methane feedstock to benzene and hydrogen via a dehydroaromatization reaction. The dehydroaromatization step can be conducted in one or more fixed beds, moving beds, or fluidized bed reactors, with catalyst regeneration being conducted in-situ or ex-situ with air, oxygen, carbon dioxide, carbon monoxide, water, $H_2$, or combinations thereof.

The dehydroaromatization reaction is endothermic and, hence when the reaction is conducted in a plurality of stages, it may be necessary to employ interstage heating to return the feed to the required reaction temperature. The fuel required to provide the interstage heating may be obtained by removing and combusting a sidestream from the dehydroaromatization effluent, after separation of the aromatic components and/or alkylated aromatic components. In addition, when the reaction occurs in the presence of a moving bed of catalyst, a portion or all of the heat may be supplied by withdrawing a portion of the catalyst from the bed, heating the catalyst by, for example, combustion of coke on the catalyst and then returning the heated catalyst to the moving catalyst bed.

The major components of the effluent from the dehydroaromatization step are $H_2$, benzene, carbon monoxide, ethylene, and residual methane. Typically, the effluent contains a concentration of aromatic rings which is at least 5 weight percent (wt %), or at least 10 wt %, or at least 15 wt %, or at least 20 wt % greater than the concentration of aromatic rings in the feed.

The benzene and aromatics may then be recovered from the dehydroaromatization effluent, for example, by solvent extraction followed by fractionation. After recovery of the aromatic hydrocarbons from the dehydroaromatization effluent, the hydrogen and unreacted methane in the effluent are reacted with $CO_2$, and/or $H_2O$, to produce synthesis gas (typically referred to herein as syngas).

The subject matter of U.S. Pat. No. 7,772,450 is incorporated by reference herein in its entirety.

Syngas Generation Via Reforming

To generate syngas by reforming, hydrocarbon feeds may be converted to a mixture of $H_2$, CO, and $CO_2$ by reacting hydrocarbons with steam in the presence of a catalyst. Any conventional reforming type catalyst can be used, but generally the catalyst comprises at least one active metal or metal oxide of Group 6 or Groups 8-10 of the Periodic Table of the Elements. Any conventional reformer can be used in the step of catalytic steam reforming. The use of a tubular reformer may be preferred. Steam reforming is generally carried out at superatmospheric pressure. The ratio of steam to hydrocarbon feed may vary depending on the overall conditions in the reformer. The amount of steam employed is influenced by the requirement of avoiding carbon deposition on the catalyst, and by the acceptable methane content of the effluent at the reforming conditions maintained.

Syngas Generation Via Carbon Dioxide Reforming or Dry Reforming

Dry reforming is the reaction of carbon dioxide with a hydrocarbon to form carbon monoxide and hydrogen. The reaction may be carried out in the presence of a catalyst. Any conventional reforming type catalyst can be used. Any conventional reformer configuration can be used in the step of catalytic dry reforming. The use of a tubular reformer may be preferred. Dry reforming is generally carried out at superatmospheric pressure. The ratio of carbon dioxide to hydrocarbon feed may vary depending on the overall conditions in the reformer. The amount of carbon dioxide employed may be influenced by the requirement of avoiding carbon deposition on the catalyst, and by the acceptable methane content of the effluent at the reforming conditions maintained. The hydrogen to carbon oxide ratio of the syngas produced may vary depending on the overall conditions of the reformer. One or more catalysts may be used to convert the methane feedstock to benzene and hydrogen. The resultant product stream of benzene and hydrogen from the first reactor 103 is then passed through the separator and the products coming from the upstream of separator may be mixed with carbon dioxide. The carbon dioxide in the gaseous feed mixture used in certain embodiments may originate from various sources. Preferably, the carbon dioxide may come from a waste or recycle gas streams. In certain embodiments, the waste or recycle gas streams may come from a plant on the same site, such as an ammonia synthesis process, optionally with (non-catalytical) adjustment of the gas composition, or after recovering the carbon dioxide from a gas stream. Using carbon dioxide as a feedstock in the process of the invention thus contributes to reducing the amount of carbon dioxide emitted to the atmosphere (from a chemical production site).

The combined stream may then be fed to a second reactor 105. The second reactor may be a reforming reactor. The second reactor 105 may produce a product stream including syngas, water, and unconverted methane and carbon dioxide. The product stream of the second reactor 105 may be separated by one or more separators into various components. The methane may be recycled to the first reactor 103 to undergo dehydroaromatization, if desired. The synthetic gas in the product stream of the second reactor 105 may be routed to a subsequent reactor 109 for conversion to methanol. The subsequent reactor 109 may be a methanol synthesis reactor. Processes for conversion of syngas to methanol and butanals are well-known to one of ordinary skill in the art. Subsequent reactors may also be DME synthesis reactors 110 and/or hydroformylation reactors 111. The product stream of the second reactor can feed into one or more subsequent reactors.

The processes disclosed herein include at least the following embodiments:

Embodiment 1

A process for producing aromatics and other chemicals, the process comprising: providing methane to a first reactor to produce a first product stream comprising benzene and hydrogen; recovering benzene from the first product stream and mixing the remaining first product stream with a carbon dioxide or steam feed stream to create a combined product stream; providing the combined product stream comprising methane, C2's, C3's, and carbon dioxide or steam to a second reactor to produce a second product stream comprising synthesis gas, water, unconverted methane and carbon dioxide; and providing the synthesis gas to a third reactor to produce a third product stream comprising methanol, butanal, olefins, or dimethyl ether.

Embodiment 2

The process of claim 1, wherein the first reactor produces the first product stream by dehydroaromatization.

Embodiment 3

The process of claim 1 or claim 2, wherein the second reactor is a reforming reactor.

Embodiment 4

The process of any of claims 1-3, wherein the third reactor is a methanol synthesis reactor, hydroformylation reactor, or dimethyl ether synthesis reactor.

Embodiment 5

The process of claim 3, wherein the third reactor is a methanol synthesis reactor.

Embodiment 6

The process of claim 3, wherein the third reactor is a hydroformylation reactor.

Embodiment 7

The process of claim 3, wherein the third reactor is a dimethyl ether synthesis reactor.

Embodiment 8

The process of any of claims 1-7, wherein the benzene is recovered from the first product stream prior to entering the second reactor.

Embodiment 9

The process of any of claims 1-8, wherein the carbon dioxide or steam feed stream is a carbon dioxide feed stream.

Embodiment 10

The process of any of claims 1-8, wherein the carbon dioxide or steam feed stream is a steam feed stream.

Embodiment 11

The process of any of claims 1-10, further comprising adding a propylene feed stream to the third reactor, wherein the third reactor is a hydroformylation reactor.

Embodiment 12

The process of any of claims 1-11, wherein methane feed to the first reactor contains less than 100 ppm each of nitrogen and sulfur compounds.

Embodiment 13

The process of any of claims 1-12, wherein methane feed to the first reactor comprises 95 mol percent methane.

Embodiment 14

The process of any of claims 1-13, wherein the first product stream contains a contains a concentration of aromatic rings that is at least 5 weight percent greater than a concentration of aromatic rings in the methane feed to the first reactor.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The disclosed subject matter is not to be limited in scope by the specific embodiments described herein. Indeed, various modifications in addition to those described herein will become apparent to those skilled in the art from the foregoing description. Such modifications are intended to fall within the scope of the appended claims.

What is claimed is:

1. A process for producing aromatics and other chemicals, the process comprising:
   providing methane to a first reactor to produce a first product stream comprising benzene and hydrogen;
   recovering benzene from the first product stream and mixing the remaining first product stream with a carbon dioxide or steam feed stream to create a combined product stream;
   providing the combined product stream comprising methane, C2's, C3's, and carbon dioxide or steam to a second reactor to produce a second product stream comprising synthesis gas, water, unconverted methane and carbon dioxide; and
   providing the synthesis gas to a third reactor to produce a third product stream comprising methanol, butanal, olefins, or dimethyl ether;
   wherein the third reactor is a hydroformylation reactor.

2. The process of claim 1, wherein the first reactor produces the first product stream by dehydroaromatization.

3. The process of claim 1, wherein the second reactor is a reforming reactor.

4. The process of claim 1, wherein the benzene is recovered from the first product stream prior to entering the second reactor.

5. The process of claim 1, wherein the carbon dioxide or steam feed stream is a carbon dioxide feed stream.

6. The process of claim 1, wherein the carbon dioxide or steam feed stream is a steam feed stream.

7. The process of claim 1, further comprising adding a propylene feed stream to the third reactor.

8. The process of claim 1, wherein methane feed to the first reactor contains less than 100 ppm each of nitrogen and sulfur compounds.

9. The process of claim 1, wherein methane feed to the first reactor comprises 95 mol percent methane.

10. The process of claim 1, wherein the first product stream contains a concentration of aromatic rings that is at least 5 weight percent greater than a concentration of aromatic rings in the methane feed to the first reactor.

\* \* \* \* \*